Figure 1:
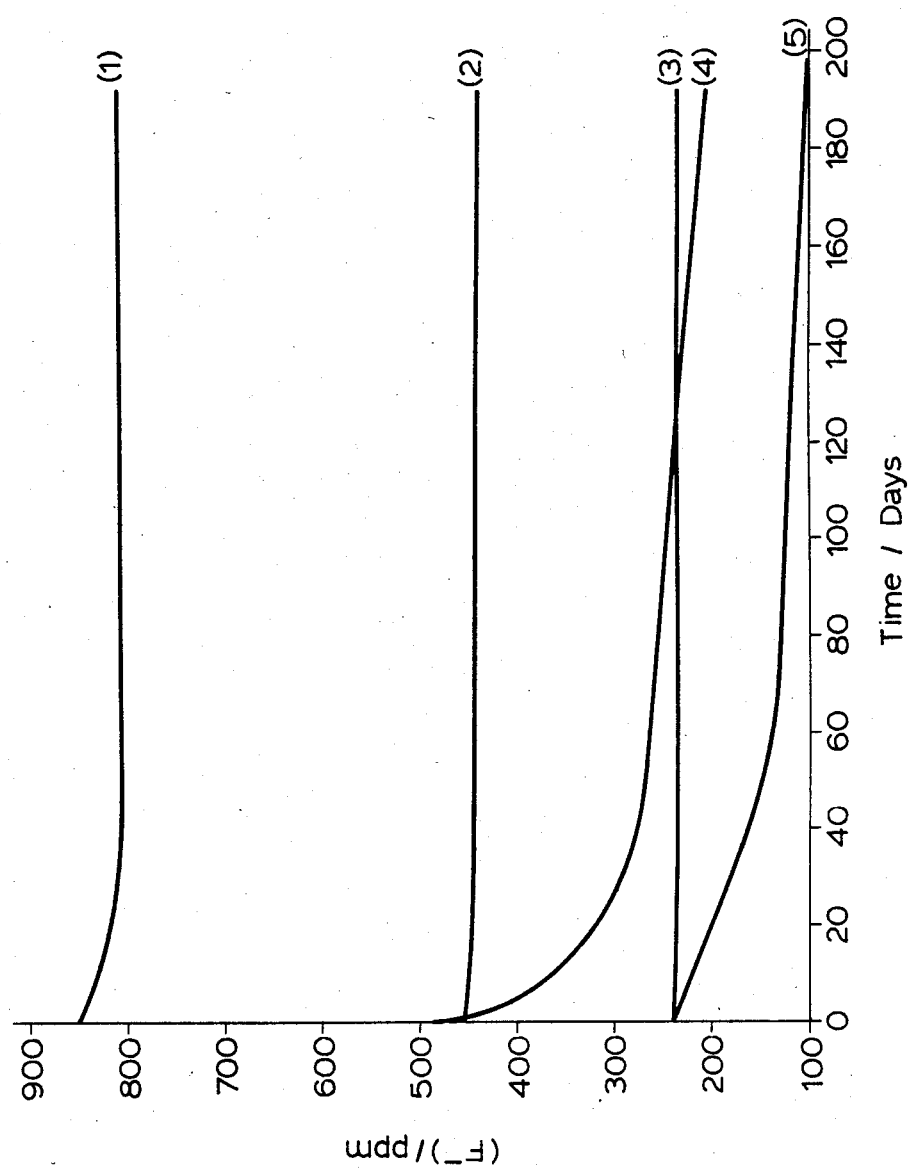

United States Patent [19]

Jackson

[11] Patent Number: 4,565,691

[45] Date of Patent: Jan. 21, 1986

[54] ORAL HYGIENE COMPOSITIONS

[75] Inventor: Robert J. Jackson, Leatherhead, England

[73] Assignee: Beecham Group p.l.c., England

[21] Appl. No.: 485,609

[22] Filed: Apr. 18, 1983

[30] Foreign Application Priority Data

Apr. 20, 1982 [GB] United Kingdom ............... 8211343

[51] Int. Cl.$^4$ .......................... A61K 7/16; A61K 7/18
[52] U.S. Cl. ...................................... 424/52; 424/49; 424/57
[58] Field of Search .................................. 424/49–58

[56] References Cited

U.S. PATENT DOCUMENTS

| 3,937,804 | 2/1976 | Delaney et al. | 424/52 |
| 4,048,300 | 9/1977 | Tomlinson et al. | 424/52 |
| 4,108,980 | 8/1978 | Duff | 424/52 |
| 4,174,387 | 11/1979 | Cordon et al. | 424/52 |

FOREIGN PATENT DOCUMENTS 1222197 of 1971 United Kingdom .
2068727 of 1981 United Kingdom .

Primary Examiner—Shep K. Rose
Attorney, Agent, or Firm—Jacobs & Jacobs

[57] ABSTRACT

An oral hygiene composition comprises from 0.01 to 2.0% by weight of the composition of a water soluble ionic fluoride, an ionic abrasive material containing metal cations capable of forming a water insoluble fluoride, and between 0.01% and 9% by weight of the composition of a water soluble ionic agent containing the anionic counter ions of the ionic abrasive together with metal cations capable of forming a water soluble fluoride. The composition is useful in reducing or preventing the inactivation of a water soluble ionic fluoride by an ionic abrasive material.

8 Claims, 2 Drawing Figures

ORAL HYGIENE COMPOSITIONS

This invention relates to oral hygiene compositions having anti-cariogenic activity.

Hitherto, it has been well known to incorporate a wide variety of fluoride compounds into oral hygiene compositions such as dentifrices in order to provide them with anti-cariogenic activity. This activity is believed to result from the effect of the fluoride compound in reducing the solubility of tooth enamel in weakly acidic media such as often occurs in the mouth owing to the action of bacteria on foods. The effect of reducing the solubility of dental enamel is believed to result from an interaction of hydroxyapatite, the mineral which constitutes the major part of dental enamel, with the fluoride to produce fluoroapatite. Fluorapatite has a lower solubility in a weakly acidic medium than hydroxyapatite.

While sodium fluoride was one of the first fluorides advocated for addition to dentifrices, it has found relatively little use because it has long been believed that the calcium-containing abrasives often used in dentifrices, especially calcium carbonate, are incompatible with ionic fluorides such as sodium fluoride. Thus it was long ago reported that the anti-cariogenic effect of sodium fluoride was inhibited by the presence of calcium carbonate, no doubt because it was believed that these substances would primarily interact to produce the insoluble and inactive calcium fluoride. For this reason, sodium monofluorophosphate has often been used instead of sodium fluoride.

We have now found a method of reducing or preventing the inactivation of water soluble ionic fluorides, such as sodium fluoride, by calcium carbonate and/or other dentifrice additives which contain metal cations capable of forming insoluble fluorides.

Accordingly, the present invention provides an oral hygiene composition comprising from 0.01 to 2.0% by weight of the composition of a water soluble ionic fluoride, an ionic abrasive material containing metal cations capable of forming a water insoluble fluoride and between 0.01% and 9% by weight of the composition of a water soluble ionic agent containing the anionic counter ions of the ionic abrasive together with metal cations capable of forming a water soluble fluoride.

The term 'anionic counter ions' is used herein to mean anions which are identical to those in the abrasive, or the same anions modified by hydrogenation.

The term 'water soluble ionic fluoride' is used herein to include any ionic material which, in aqueous solution, provides fluoride or monofluorophosphate ions. The use of an alkali-metal fluoride is preferred, such as sodium, potassium or lithium fluoride; the use of sodium fluoride is especially preferred. Other suitable fluorides include ammonium, stannous and zinc fluorides.

Alternatively, a monofluoro-phosphate is used, preferably an alkali metal monofluoro-phosphate. Sodium monofluorophosphate, $Na_2PO_3F$, is especially preferred but the corresponding potassium and/or lithium salts can also be employed. The term 'monofluorophosphate' as used herein includes monofluoropolyphosphates, such as those of formulae $Na_4P_3O_9F$; $K_4P_3O_9F$; $Na_3KP_3O_9F$; $(NH_4)_3NaP_3O_9F$ and $Li_4P_3O_9F$.

If desired, a mixture of ionic fluoride and monofluorophosphate may be employed. The total amount of fluoride and monofluorophosphate used is dependent to some extent on the type of dentifrice composition, but it should be an effective, but non-toxic, amount. Typically the fluoride(s) is present in the oral hygiene composition in an amount to provide a total of from 0.025 to 0.25% of fluorine based on the weight of the oral hygiene composition. The preferred total fluoride level is from 0.05 to 0.15% by weight of the composition.

Suitable abrasive materials include insoluble carbonates and phosphates.

Preferably, the abrasive material is calcium carbonate, in which case the preferred ionic agent is a soluble carbonate or bicarbonate, such as an alkali metal carbonate or bicarbonate, preferably sodium carbonate. Alternatively, the abrasive material is a calcium phosphate, such as dicalcium phosphate, in which case the preferred ionic agent is a soluble phosphate or hydrogen phosphate such as an alkali metal hydrogen phosphate, for example dipotassium hydrogen phosphate.

The preferred amount of water soluble ionic agent present is from 0.5% to 6%, more preferably about 5% to 6%.

A particularly preferred agent is a sodium carbonate/bicarbonate mixture in which the bicarbonate is in excess over the carbonate. A preferred mixture consists of about 5% sodium bicarbonate and 0.5% sodium carbonate, by weight of the composition.

The ionic agent is preferably present in the composition of the invention in the form of an aqueous solution so that it has no abrasive character of its own.

The preferred dental abrasive, calcium carbonate, can be in either of the geological forms known as Aragonite and Calcite or a mixture of the two. Other forms of calcium carbonate include powdered limestone and milled marble or mined powder products. Preferably the calcium carbonate should have a weight median diameter of less than 40 microns.

Other dental abrasives may also be present instead of or in admixture with calcium carbonate.

For instance there may be employed water-insoluble sodium or potassium metaphosphates, hydrated or anhydrous dicalcium phosphate, calcium pyrophosphate, aluminium trihydrate, tricalcium phosphate, calcium silicate, zirconium silicate or mixtures thereof. Particularly useful polishing agents are various forms of silica, especially silica xerogels as defined in U.S. Pat. No. 3,538,230, though such xerogels may have an average particle size diameter up to 50 microns. The abrasive(s) may be employed in a total amount of from 10 to 99% by weight of the composition of the invention. Preferably such compositions are in the form of dentifrice pastes containing 20 to 75% of dental abrasive, though they can be in the form of powders containing 70 to 99% of the abrasive. If desired, the compositions of the invention can be formulated as striped dentifrice compositions, such as those described in U.K. Patent Specification No. 1271944.

The oral hygiene compositions of the invention will also usually contain surfactants, gelling agents and other excipients such as flavouring and colouring agents.

The surfactant is normally a water-soluble non-soap or synthetic organic detergent. Suitable surfactants include the water-soluble salts of: higher fatty acid monoglyceride monosulphates (for example sodium hydrogenated coconut fatty acid monoglyceride monosulphate); higher alkyl sulphates (for example sodium lauryl sulphate); alkylarylsulphonates (for exmple sodium dodecylbenzenesulphonates); and higher alkyl sulphoacetates (for example sodium lauryl sulphoacetate). There may also be used the saturated higher aliphatic acyl amides of lower aliphatic amino carboxylic acids having 12 to 16 carbon atoms in the acyl radical and in which the amino acid portion is derived from the lower aliphatic saturated monoaminocarboxylic acids having 2 to 6 carbon atoms, such as the fatty acid amides of glycine, sarcosine, alanine, 3-aminopropanoic acid and valine, particularly the N-lauroyl, myristoyl and palmitoyl sarcosinate compounds. Conventional non-ionic surfactants may also be included, if desired.

The surface-active materials are generally present in an amount of 0.05 to 15%, preferably 0.5 to 5% by weight of the composition.

The tooth powders and pastes are prepared in the usual manner. Thus, the ingredients can be mixed in the dry state or as slurries or solutions.

In general the liquids in the dental cream or paste will comprise chiefly water, glycerine, sorbitol and/or a glycol, including suitable mixtures thereof. Suitably, the glycol is propylene glycol or a polyethylene glycol. It is preferred to use also a gelling agent in dental creams, such as natural or synthetic gums or gum-like materials, e.g. Irish Moss, gum tragacanth, sodium carboxymethylcellulose, polyvinylpyrrolidone or starch. Irish Moss and sodium carboxymethylcellulose are preferred gelling agents. The gum content is usually up to 10% and preferably 0.01 to 5% by weight of the preparation.

The pH of the dental cream or an aqueous slurry of the tooth powder is neutral to slightly basic, such as a pH of about 7-11. Typically the pH is about pH 8.5 to 9.5.

Other materials may be added, such as sweetening agents, for example soluble saccharin, flavouring oils (e.g. oils of spearmint, wintergreen, peppermint), chloroform, colouring or whitening agents (e.g. titanium dioxide), preservative (e.g. sodium benzoate), emulsifying agents, silicones, alcohol, menthol, chlorophyll compounds (e.g. sodium copper chlorophyllin), anti-bacterial agents (e.g. chlorhexidine), anti-plaque agents, anti-calculus agents, agents for sensitive dentine (e.g. strontium salts, formaldehyde), and agents which enhance the anti-caries activity of fluorides (e.g. calcium glycerophosphate).

The compositions of the invention may also be in a form of other oral hygiene compositions, for example, the ingredients may be incorporated in mouth washes of the suspension type, or in compositions which will be chewed by the user, for example, chewing gum, tablets, pastilles and lozenges. These compositions will contain the conventional base materials together with suitable flavours and sweetening agents and may be formulated in known manner.

The compositions of the invention are illustrated by the following examples:

| FORMULATION | EXAMPLE NO (% BY WEIGHT) | | | | |
|---|---|---|---|---|---|
|  | 1 | 2 | 3 | 4 | 5 |
| Glycerin | 4.00 | — | 4.00 | 4.00 | — |
| 70% sorbitol | 16.00 | 30.00 | 16.00 | 16.00 | 30.00 |
| Soluble saccharin | 0.42 | 0.42 | 0.42 | 0.42 | 0.42 |
| Sodium carboxy methyl cellulose | 1.50 | 1.30 | 0.85 | 1.50 | 1.30 |
| Hydroxy ethyl cellulose | 0.10 | 0.10 | 0.10 | 0.10 | 0.10 |
| Calcium silicate | 0.20 | — | — | — | — |
| Polyvinylpyrrolidine | 0.10 | 0.10 | 0.10 | 0.10 | 0.10 |
| Calcium glycerophosphate | 0.13 | 0.13 | — | — | 0.065 |

-continued

| FORMULATION | EXAMPLE NO (% BY WEIGHT) | | | | |
|---|---|---|---|---|---|
| Sodium monofluorphosphate | 0.40 | 0.55 | — | — | 0.20 |
| Sodium fluoride | 0.115 | 0.16 | 0.22 | 0.11 | 0.0575 |
| Sodium carbonate | 2.50 | 0.50 | 8.00 | 2.00 | 0.25 |
| Calcium carbonate | 36.22 | 35.00 | 36.22 | 36.22 | 35.00 |
| Sodium lauryl sulphate | 1.88 | 1.88 | 1.88 | 1.88 | 1.88 |
| Hydrated silicon dioxide | 4.00 | 3.25 | 4.00 | 4.00 | 3.25 |
| Flavour | 1.00 | 1.15 | 1.00 | 1.00 | 1.15 |
| Titanium dioxide | — | 0.50 | 0.50 | 0.50 | 0.50 |
| Sodium bicarbonate | — | 5.00 | — | — | 2.50 |
| Water to | 100.00 | 100.00 | 100.00 | 100.00 | 100.00 |

|  | 6 | 7 |
|---|---|---|
| 70% Sorbitol | 10.00 | 15.00 |
| Glycerin | 10.00 | 10.00 |
| Sodium carboxy methyl cellulose | 1.20 | 1.15 |
| Soluble saccharin | 0.30 | 0.35 |
| Disodium hydrogen phosphate | 1.00 | — |
| Sodium di-hydrogen phosphate | — | 0.75 |
| Sodium monofluorophosphate | 0.76 | 0.40 |
| Sodium fluoride | 0.10 | 0.11 |
| Dicalcium phosphate dihydrate | 46.00 | — |
| Insoluble sodium metaphosphate | — | 38.00 |
| Sodium lauryl sulphate | 1.60 | 1.80 |
| Flavour | 0.95 | 1.10 |
| Water to | 100.00 | 100.00 |

The following Example 8 is a striped toothpaste composition made in accordance with U.K. Patent Specification No. 1271944.

| Example 8 | | |
|---|---|---|
|  | Secondary body | Main Body |
| 70% Sorbitol Solution | 35.5 | 60.00 |
| Hydrated silicon dioxide | 5.00 | 15.00 |
| Polyethylene glycol | 2.95 | 3.00 |
| Sodium carboxymethyl cellulose | 0.60 | 1.30 |
| Sodium lauryl sulphate | 1.20 | 1.20 |
| Flavour | 0.85 | 0.85 |
| Soluble saccharin | 0.13 | 0.27 |
| Titanium dioxide | 0.50 | — |
| Calcium glycerophosphate | 0.13 | 0.13 |
| Sodium monofluorophosphate | 0.76 | 0.76 |
| Sodium fluoride | 0.22 | 0.22 |
| Calcium carbonate | 42.00 | — |
| Sodium bicarbonate | 3.40 | 6.00 |
| Sodium carbonate | 0.34 | 0.60 |
| Colour | — | qs |
| Water to | 100.00 | |

Ratio of main body to secondary body is 62:38

The efficacy of the invention is illustrated by the following experiments carried out on the dissolution rate of hydroxyapatite. This is an appropriate model since it corresponds to the mineral composition of tooth enamel and is dissolved by the action of dilute acids such as those formed in the mouth from decaying food.

Discs of hydroxyapatite were prepared by blending it with 10% of polyethylene to improve binding characteristics followed by moulding separate discs by compression at 500 kg for 90 seconds and subsequent heating to 110° C. Separate discs were treated with a slurry of the dentifrice to be tested with water (water:dentifrice=3:1) for one minute. The dentifrice composition had been stored for 2 weeks after its preparation and was of the general composition of that of Example 1.

The treated hydroxyapatite discs were each placed beneath a rotating propeller in acetic acid buffer at pH 4.65 and at 37° C. for one hour. Aliquots were removed at 5 min intervals. The dissolution rate constant, k, was calculated using the following equation:

$$\frac{dC}{dt} = k(C_\alpha - C_t)$$

wherein $C_\infty$ is the concentration at infinite time;
$C_t$ is the concentration at time t.
and
dC/dt is the rate of change in the concentration, C, with respect to time, t. The percentage change in the rate constant relative to treatment with an identical dentifrice or solution but containing no fluoride ws determined.

The results are set out below:

| DISSOLUTION RATE DATA | |
|---|---|
| TREATMENT | % CHANGE IN DISSOLUTION RATE |
| Distilled water | — |

Dentifrice having general composition of Example 1. and containing:

| | | | |
|---|---|---|---|
| (i) | 0.11% | Sodium fluoride | 63 |
| | 0.40% | Sodium monofluorophosphate | |
| | 2.5% | Sodium carbonate | |
| (ii) | 0.055% | Sodium fluoride | 55 |
| | 0.20% | Sodium monofluorophosphate | |
| | 2.5% | Sodium carbonate | |

The effect of the incorporation of a water soluble ionic agent, such as sodium carbonate, or dipotassium hydrogen phosphate, on stabilising ionic fluorides is illustrated by the following experiments.

Slurries containing chalk (40 g) in de-ionised water (100 ml) were stabilised with varying quantities of sodium carbonate prior to the addition of known quantities of sodium fluoride, and then stored at room temperature for a period of 190 days. The available fluoride ion concentration was monitored, see FIG. 1, in compositions containing 8% (1); 2% (2); 0.5% (3) and 0% [(4) and (5)] sodium carbonate by weight.

FIG. 1, clearly shows that the available fluoride ion concentration decreases when no sodium carbonate was added [(4) and (5)]. However, the available fluoride ion concentration (i.e. [F$^-$]) shows little instability when 0.5% sodium carbonate is added (3) to a slurry containing 250 ppm [F$^-$]. Likewise, the inactivation of sodium fluoride is also prevented by higher concentrations of sodium carbonate, as shown by the use of 2% sodium carbonate slurry containing 450 ppm [F$^-$] (2) and 8% sodium carbonate slurry containing 850 ppm [F$^-$] (1).

Figure 2:
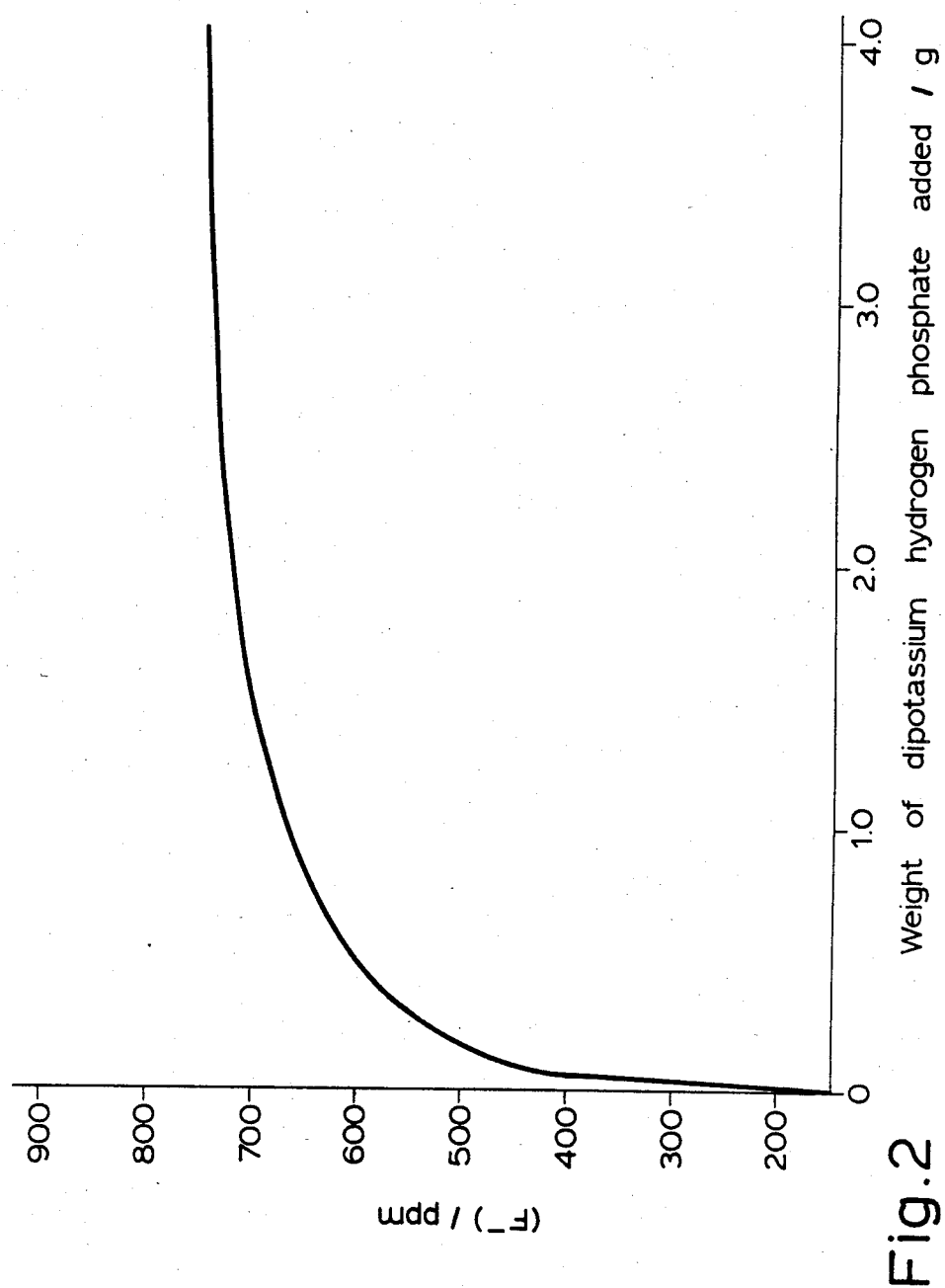

A slurry of dicalcium phosphate (10 g) and sodium fluoride (0.44 g, ie 1000 ppm [F$^-$], weight/volume) in distilled water (200 ml) was stabilized by the addition of varying amounts of dipotassium hydrogen phosphate. Each slurry was stored for 4 days prior to measuring the ionic fluoride concentration. Optimum results were obtained on addition of above 2 g of dipotassium hydrogen phosphate; a stable fluoride ion concentration of between 725 to 750 ppm was observed (FIG. 2).

I claim:

1. An oral hygiene composition, comprising from 0.01 to 2.0% by weight of the composition of a water soluble fluoride source consisting of an ionic fluoride or an ionic fluoride admixed with an ionic monofluorophosphate, from 10 to 99% by weight of the composition of a water insoluble ionic abrasive material containing metal cations capable of forming a water insoluble fluoride, and between 0.01% and 9% by weight of the composition of a water soluble ionic agent containing the anionic counter ions of the ionic abrasive together with metal cations capable of forming a water soluble fluoride.

2. A composition according to claim 1, in which the fluoride source consists of an alkali metal fluoride or a mixture of an alkali metal fluoride and an alkali metal monofluorophosphate.

3. A composition according to claim 1, in which the water soluble ionic agent is present in an amount of from 0.5% to 6% by weight of the composition.

4. A composition according to claim 1, in the form of a dentifrice.

5. An oral hygiene composition comprising from 0.01 to 2.0% by weight of the composition of a water soluble fluoride source consisting of an ionic fluoride or an ionic fluoride admixed with an ionic monofluorophosphate, from 10 to 99% by weight of the composition of calcium carbonate and between 0.01% and 9% by weight of the composition of an alkali metal carbonate or bicarbonate or mixture thereof.

6. A composition according to claim 5, in which the fluoride source consists of an alkali metal fluoride or a mixture of an alkali metal fluoride and an alkali metal monofluorophosphate.

7. A composition according to claim 5, in which the alkali metal carbonate or bicarbonate is present in an amount of from 0.5% to 6% by weight of the composition.

8. A composition according to claim 5, in the form of a dentifrice.

* * * * *